(12) United States Patent
Au et al.

(10) Patent No.: US 11,523,202 B2
(45) Date of Patent: Dec. 6, 2022

(54) HEARING DEVICES INCLUDING BIOMETRIC SENSORS AND ASSOCIATED METHODS

(71) Applicant: Sonova AG, Stäfa (CH)

(72) Inventors: Michael Au, Union City, CA (US); Frank Wang, San Bruno, CA (US); Grace Gardner, San Leandro, CA (US); Lu Zhang, San Jose, CA (US); Stephan Gehring, Uerikon (CH); Daniel Baer, Zurich (CH)

(73) Assignee: Sonova AG, Staefa (CH)

( * ) Notice: Subject to any disclaimer, the term of this patent is extended or adjusted under 35 U.S.C. 154(b) by 160 days.

(21) Appl. No.: 16/922,221

(22) Filed: Jul. 7, 2020

(65) Prior Publication Data

US 2022/0014834 A1   Jan. 13, 2022

(51) Int. Cl.
| | |
|---|---|
| *H04R 25/00* | (2006.01) |
| *H04R 1/10* | (2006.01) |
| *H04R 25/02* | (2006.01) |
| *A61B 5/00* | (2006.01) |
| *A61B 5/145* | (2006.01) |
| *A61B 5/024* | (2006.01) |
| *A61B 5/0533* | (2021.01) |
| *A61B 5/021* | (2006.01) |
| *A61B 5/318* | (2021.01) |

(52) U.S. Cl.
CPC ......... *H04R 1/1016* (2013.01); *A61B 5/6817* (2013.01); *H04R 1/105* (2013.01); *H04R 1/1041* (2013.01); *H04R 25/02* (2013.01); *A61B 5/021* (2013.01); *A61B 5/02405* (2013.01); *A61B 5/0533* (2013.01); *A61B 5/14542* (2013.01); *A61B 5/14546* (2013.01); *A61B 5/318* (2021.01); *A61B 5/4875* (2013.01)

(58) Field of Classification Search
CPC .... H04R 1/1016; H04R 1/1041; H04R 1/105; H04R 25/02; A61B 5/6817
See application file for complete search history.

(56) References Cited

U.S. PATENT DOCUMENTS

| | | | |
|---|---|---|---|
| 6,004,274 A | 12/1999 | Nolan et al. | |
| 8,630,432 B2 | 1/2014 | Rass | |
| 8,702,607 B2 | 4/2014 | LeBoeuf et al. | |
| 9,794,668 B2 | 10/2017 | Masaki et al. | |
| 2006/0206014 A1 | 9/2006 | Ariav | |
| 2010/0217103 A1* | 8/2010 | Abdul-Hafiz | A61B 5/02427 600/322 |
| 2015/0077245 A1* | 3/2015 | Kaufman | A61B 5/14551 340/539.12 |
| 2016/0051195 A1 | 2/2016 | Pang et al. | |
| 2016/0057550 A1* | 2/2016 | Shennib | H04R 25/554 381/315 |
| 2017/0028199 A1* | 2/2017 | Roehrlein | A61N 1/36038 |
| 2017/0095167 A1* | 4/2017 | Facteau | A61B 5/6817 |
| 2018/0116514 A1* | 5/2018 | Turner | G16H 40/63 |

(Continued)

FOREIGN PATENT DOCUMENTS

WO   WO 2018/224340 A1   12/2018

*Primary Examiner* — Simon King
(74) *Attorney, Agent, or Firm* — Henricks Slavin LLP

(57) ABSTRACT

An ITE hearing instrumentality, for use in an ear canal, that includes a housing, a receiver located within the housing, an earpiece on the housing that is configured to mount the housing within the ear canal, and at least one biometric sensor on the earpiece.

21 Claims, 7 Drawing Sheets

(56) References Cited

U.S. PATENT DOCUMENTS

| | | | |
|---|---|---|---|
| 2018/0184907 A1* | 7/2018 | Tran | H04M 3/5116 |
| 2018/0376264 A1* | 12/2018 | Roeck | B01D 61/427 |
| 2019/0090071 A1* | 3/2019 | Mazzucchi | H04R 25/55 |
| 2019/0174238 A1* | 6/2019 | Lu | A61B 5/0205 |
| 2019/0253793 A1* | 8/2019 | Pedersen | H04R 25/55 |
| 2019/0394584 A1* | 12/2019 | Nikles | H04R 25/552 |
| 2020/0186904 A1* | 6/2020 | Krull | H04R 1/1041 |
| 2020/0196073 A1* | 6/2020 | Nielsen | A61B 5/6817 |
| 2020/0213787 A1* | 7/2020 | Houcek | H04R 25/48 |
| 2020/0268260 A1* | 8/2020 | Tran | A61B 5/6817 |
| 2021/0000370 A1* | 1/2021 | Mirov | A61B 5/6803 |
| 2021/0044910 A1* | 2/2021 | Kuipers | H04R 25/652 |
| 2021/0067863 A1* | 3/2021 | Shinmen | H04R 1/1016 |
| 2021/0092530 A1* | 3/2021 | Thomsen | H04R 25/50 |
| 2021/0093255 A1* | 4/2021 | Mueller | A61B 5/30 |
| 2021/0099811 A1* | 4/2021 | Roeck | H04R 25/652 |
| 2021/0099813 A1* | 4/2021 | Spieler | H04R 25/558 |
| 2021/0099815 A1* | 4/2021 | Silberzahn | A61B 5/6815 |
| 2021/0100507 A1* | 4/2021 | Kimmig | A61B 5/6843 |
| 2021/0145351 A1* | 5/2021 | Robertson | A61B 5/291 |
| 2021/0306772 A1* | 9/2021 | Wiss | G10L 25/51 |
| 2021/0360354 A1* | 11/2021 | Rasmussen | H04R 25/554 |
| 2022/0015703 A1* | 1/2022 | Mirov | A61B 5/291 |

\* cited by examiner

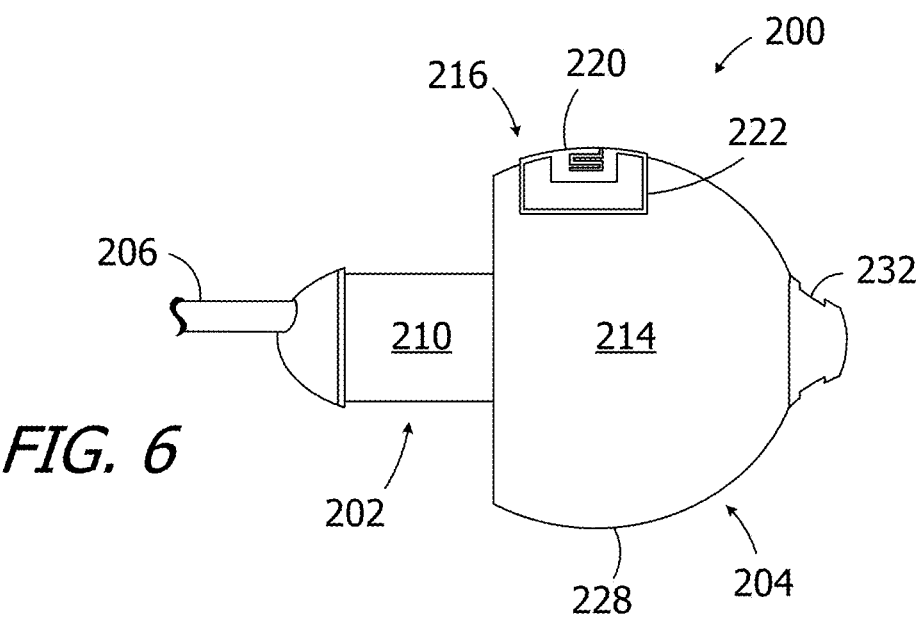
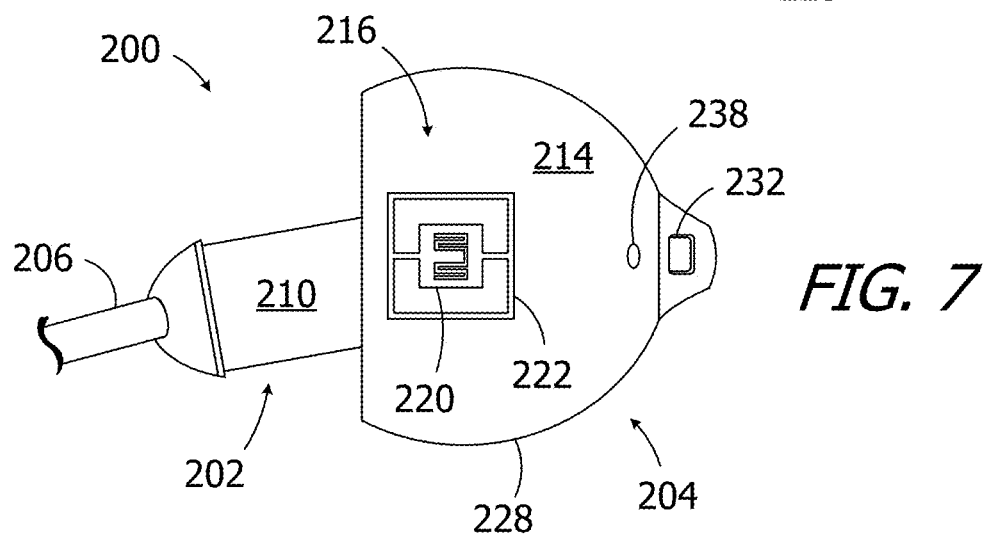
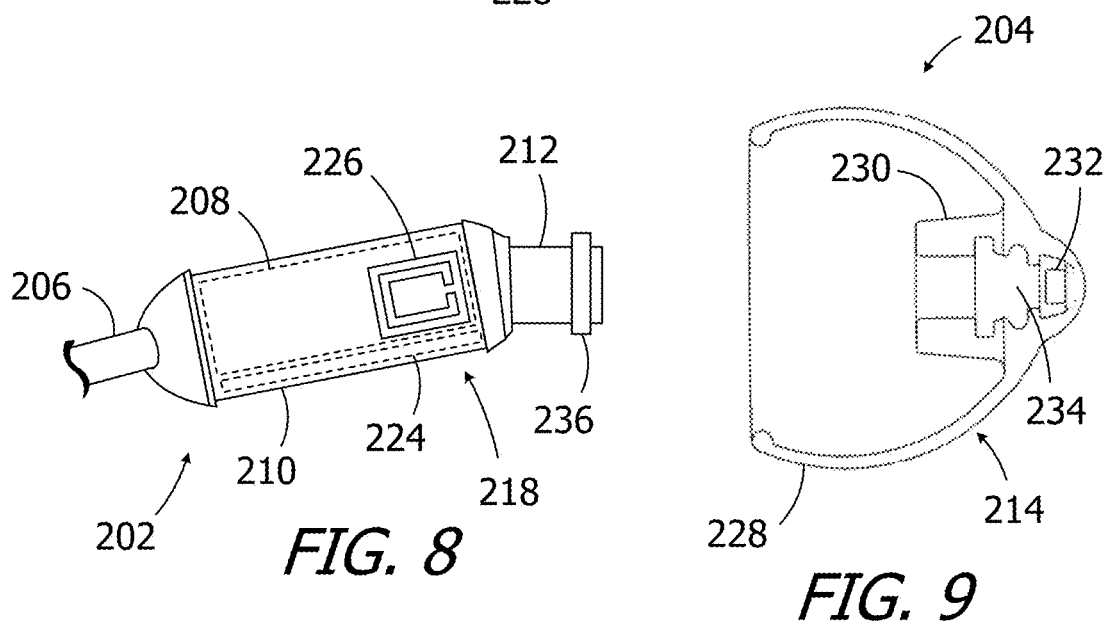

HEARING DEVICES INCLUDING BIOMETRIC SENSORS AND ASSOCIATED METHODS

BACKGROUND

1. Field

The present inventions relate generally to hearing devices and, for example, hearing devices that include a component that is worn in the ear canal.

2. Description of the Related Art

Many hearing devices (or portions thereof) are located within the ear canal. Behind-the-ear ("BTE") hearing devices, for example, typically include a BTE component, with the microphone, electronics, and battery, and an ITE component that delivers sound to ear canal. The ITE component may include a receiver assembly, with a housing and a receiver located within the housing, and a soft earpiece that is mounted on the receiver assembly to center the receiver assembly relative to the ear canal with the sound output port of the receiver housing facing the tympanic membrane. In-the-ear ("ITE") hearing devices, on the other hand, typically include a housing that is positioned within the ear canal and a receiver that is located within the housing. The housing has a sound output port that is positioned adjacent to the tympanic membrane and connected to the receiver output port. Other hearing device components (e.g., the microphone, electronics and battery) may, for example, be located with the housing or within a faceplate mounted onto the end of the housing opposite the sound port. In either case, ambient sound pressure waves are picked up by the microphone and converted into electrical signals. The electrical signals, in turn, are processed by sound processor circuitry. The processed signals drive the receiver, which delivers amplified (or otherwise processed) sound pressure waves to the ear canal.

SUMMARY

An ITE hearing instrumentality in accordance with at least one of the present inventions includes a housing, a receiver located within the housing, an earpiece on the housing that is configured to mount the housing within the ear canal, and at least one biometric sensor on the earpiece. The present inventions also includes hearing device with a BTE component operably connected to such a ITE hearing instrumentality.

A method in accordance with at least one of the present inventions includes the step of sensing a biomarker within an ear canal with a biometric sensor that is pressed against the ear canal by a portion of a ITE hearing instrumentality.

There are a variety of advantages associated with such apparatus and methods. By way of example, but not limitation, the present inventions allow biometric sensors to be positioned within the ear canal with a structure that, for users of ITE hearing instrumentalities, will already be located within the ear canal.

The above described and many other features and advantages of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 6 is a side view of the ITE component of the hearing system illustrated in FIG. 1.

FIG. 7 is a side view of the ITE component of the hearing system illustrated in FIG. 1.

FIG. 8 is a side view of a portion of the ITE component of the hearing system illustrated in FIG. 1.

FIG. 9 is a section view of a portion of the ITE component of the hearing system illustrated in FIG. 1.

DETAILED DESCRIPTION OF EXEMPLARY EMBODIMENTS

The following is a detailed description of the best presently known modes of carrying out the inventions. This description is not to be taken in a limiting sense, but is made merely for the purpose of illustrating the general principles of the inventions. It should also be noted that if and when used herein, the term "lateral" refers to the direction and parts of hearing devices which face away from the tympanic membrane, the term "medial" refers to the direction and parts of hearing devices which face toward the tympanic membrane, the term "superior" refers to the direction and parts of hearing devices which face the top of the head, the term "inferior" refers to the direction and parts of hearing devices which face the feet, the term "anterior" refers to the direction and parts of hearing devices which face the front of the body, and the "posterior" refers to the direction and parts of hearing devices which face the rear of the body.

The present inventors have determined that it would be desirable to position one or more biometric sensors within one or both of the ear canals. As used herein, a "biometric sensor" is a sensor that senses a biomarker, i.e., a measurable characteristic indicative of a biological process, a pathogenic process or pharmacological response to a therapeutic intervention, as opposed to a sensor that senses sound or an ambient condition such as humidity or barometric pressure. The present inventors have further determined that the ITE components of BTEs hearing devices and ITE hearing devices (collectively "ITE hearing instrumentalities") may be used as a vehicle to position biometric sensors within ear canals. There are a number of advantages associated with the use of ITE hearing instrumentalities to position biometric sensors within the ear canal. For example, the present inventions allow biometric sensors to be positioned within the ear canal with a structure that, for users of ITE hearing instrumentalities, will already be located within the ear canal. ITE hearing instrumentalities are also capable of positioning biometric sensors within the ear canal over long periods. In some instances, the biometric sensors may be relatively low cost devices that are positioned on portions of the ITE hearing instrumentalities that are intended to be periodically replaced, thereby facilitating efficient periodic replacement of the biometric sensors without additional effort. The present inventors have also determined that the soft earpieces that are part of certain ITE hearing instrumentalities may be used to carry both biometric sensors and ambient condition sensors.

Figure 1:
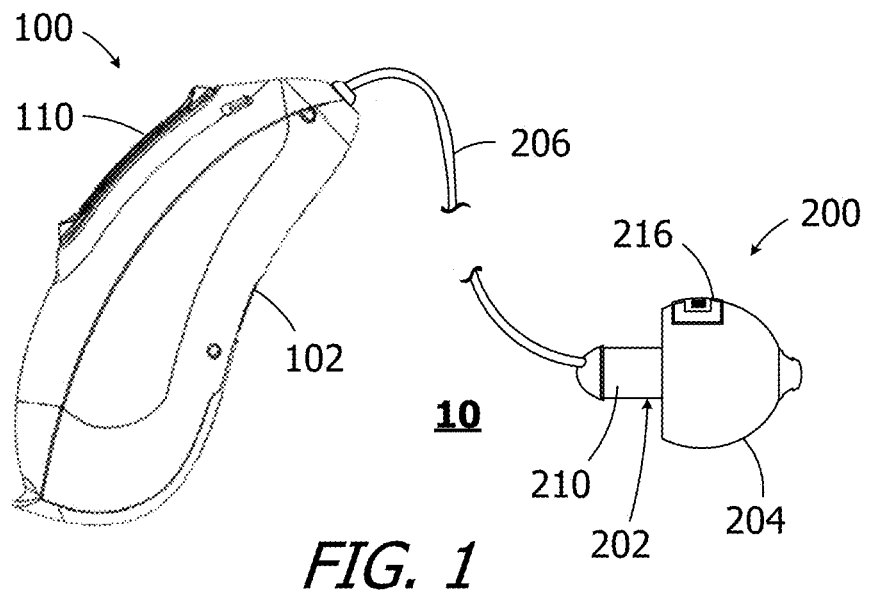
FIG. 1 is a side view of a hearing device in accordance with one embodiment of a present invention.
Figure 2:
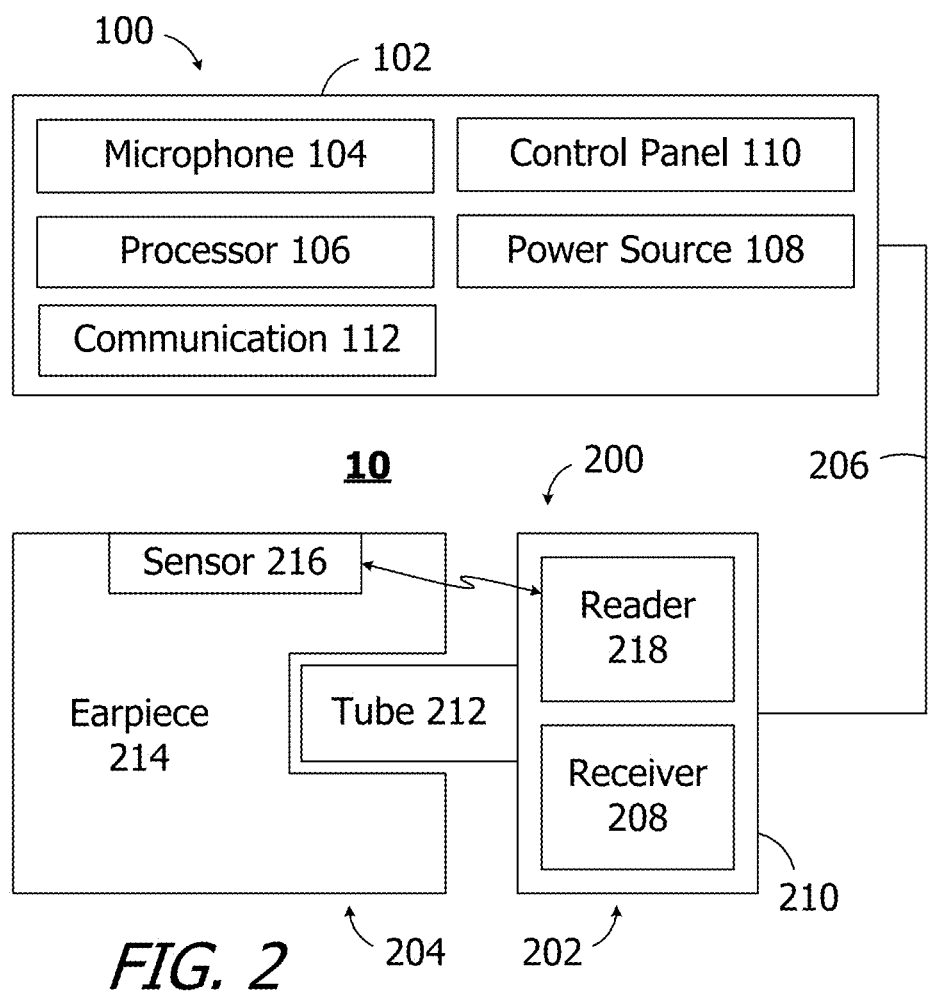
FIG. 2 is a block diagram of the hearing device illustrated in FIG. 1.

As illustrated in FIGS. 1 and 2, one example of a BTE hearing device, which is generally identified by reference numeral 10, includes a BTE component 100 that receives sound (including sound signals from another device) and an ITE component 200 that delivers sound to ear canal. The exemplary BTE component 100 may have a housing 102, one or more microphones 104, a processor 106 that may be used for sound processing and other processing functions described herein, a battery or other power source 108, a control panel 110 and other conventional instrumentalities. The various processing functions described herein may also be divided between multiple processors. Communication apparatus 112, such as an antenna and a receiver/transmitter, may be provided to allow the BTE component to communicate with external devices such as mobile phones and computers. The exemplary ITE component 200 includes a receiver assembly 202 and an earpiece assembly 204 that is mounted on the medial end of the receiver assembly 202 to center the receiver relative to the ear canal. A multi-wire cable 206, which may have connectors (not shown) on one or both ends, electrically connects the BTE component 100 to the ITE component 200. Although not so limited, the cable 206 may have eight wires in some instances, and may have four wires in some instances. The exemplary receiver assembly 202 and earpiece assembly 204 are discussed greater detail below. Briefly, the exemplary receiver assembly 202 includes a miniature loudspeaker with a sound outlet (or "receiver") 208 that is located within a receiver housing 210. A sound tube 212 extends from the receiver housing 210, and the earpiece assembly 204 is mounted on the sound tube. The exemplary earpiece assembly 204 includes a soft earpiece 214 and a biometric sensor apparatus (or "sensor apparatus") 216 that is mounted to the exterior surface of the earpiece, or the interior surface of the earpiece, or is otherwise within the earpiece. The sensor apparatus 216 may communicate with the BTE component 100 through the use of any suitable communication technique. For example, the sensor apparatus 216 may wirelessly communicate with a reader 218 that is operably connected to the BTE component 100, and various portions of the reader may be located within and/or on the receiver housing 210. In other implementations, a wired connection may be provided. Alternatively, or in addition, the reader (or at least portions thereof) may be located on or within the BTE component 100.

Figure 3:
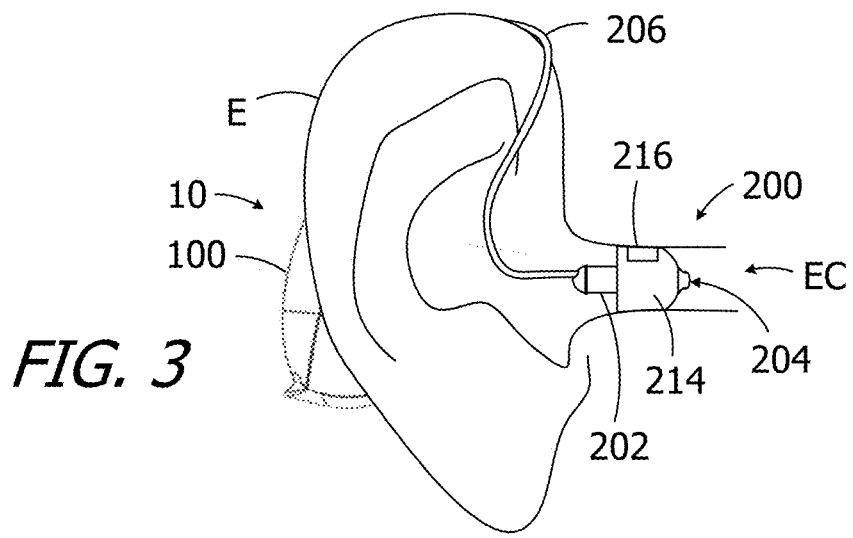
FIG. 3 is a side view showing ITE component of the hearing system illustrated in FIG. 1 within an ear.

Referring to FIG. 3, the exemplary BTE component 100 of the BTE hearing device 10 may be placed behind the ear E and the exemplary ITE component 200 may be placed within the ear canal EC. The earpiece 214 positions the sensor apparatus 216 against or adjacent to tissue within the ear canal EC. Such placement allows the sensor apparatus 216 to sense a variety of biometric markers.

Figure 4:
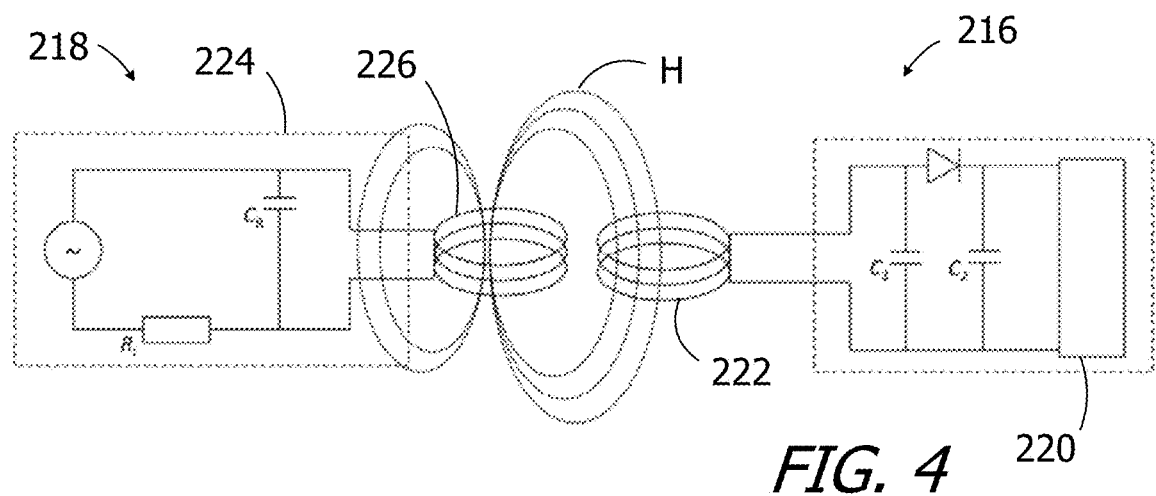
FIG. 4 is a diagram showing portions of the hearing system illustrated in FIG. 1.

The sensor apparatus 216 in at least some exemplary implementations may be in the form of a passive sensor apparatus that is powered by the reader 218. By way of example, but not limitation, the exemplary sensor apparatus 216 and reader 218 together form a radio frequency identification ("RFID") sensor arrangement. The sensor apparatus 216, which does not have an on-board power supply, receives power from the reader 218 and also transmits data to the reader through an inductive wireless coupling. Put another way, the reader 218 interrogates the passive sensor apparatus (or "transponder") 216. To that end, and referring to FIG. 4, the sensor apparatus 216 includes one or more sensors 220 (with any associated circuitry and memory), capacitors C1 and C2, and an antenna 222 (also referred to herein as a "sensor apparatus antenna") that creates a magnetic field H. The sensor(s) 220, which may be for example capacitive or resistive, may be used to sense biomarkers such as arterial pressure, arterial pulse peaks, electrical signals used in an electrocardiogram ("ECG"), electrical signals used in an electromyogram ("EMG"), heart rate, heart rate variability, oxygen level, blood pressure, hydration, core body temperature, blood glucose, galvanic skin response to determine stress or pain level, as well as the presence, absence, level or concentration of particular chemicals, enzymes, proteins or drugs. For example, in those instances where pressure is measured, the sensor 220 may be a mechanical sensor (e.g., a strain gauge). In those instances where the biomarker is the electrical signals for an ECG, the sensor 220 may be an electrical sensor such as one or more electrical contacts. A diode may also be provided in those instances where an identifier chip is employed in the sensor apparatus. The reader 218 includes an active reader circuit 224, with an RF source, a resistor Ri and a capacitor Cr, as well as an antenna 226 (also referred to herein as a "reader antenna"). The sensor apparatus 216 and the reader 218 have the same resonant frequency, which is defined by the respective antennas and capacitors.

A variety of techniques may be used to transmit biomarker data from the sensor apparatus 216 to the reader 218. Such techniques may in some instances be chosen to minimize complexity and power requirements. One example of a data transmission technique is ON-OFF-Keying ("OOK") which is a relatively simple amplitude-shift keying ("ASK") scheme. The RFID signal (or other data signal) is representative of the sensed biomarker, and does not require additional electronic processing or A/D conversion. The signal may be selectively turned ON and OFF in response to the detection of particular biomarkers or particular aspects of the biomarkers. The ON and OFF states of the signal are a function of signal frequency. A signal from the sensor apparatus antenna 222 that is sent at a frequency equal to the resonant frequency of the reader antenna 226, thereby causing the reader antenna to resonate, is considered a signal that is ON. Conversely, a signal sent from the sensor apparatus antenna 222 at a frequency that is not equal to the resonant frequency of the reader antenna 226 is considered a signal that is OFF.

Figure 5:
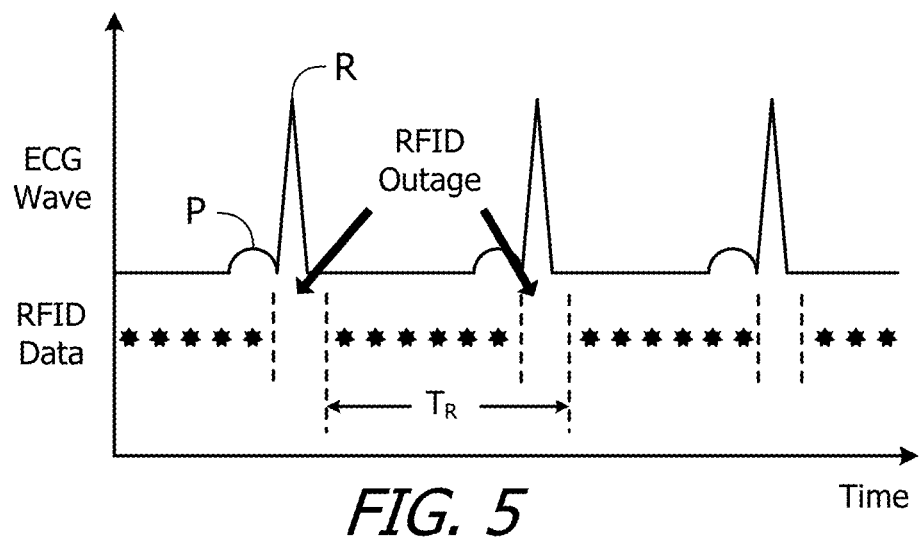
FIG. 5 is a graph showing a sensed biomarker and an exemplary communication technique that may be used by the hearing system illustrated in FIG. 1.
Figure 10:
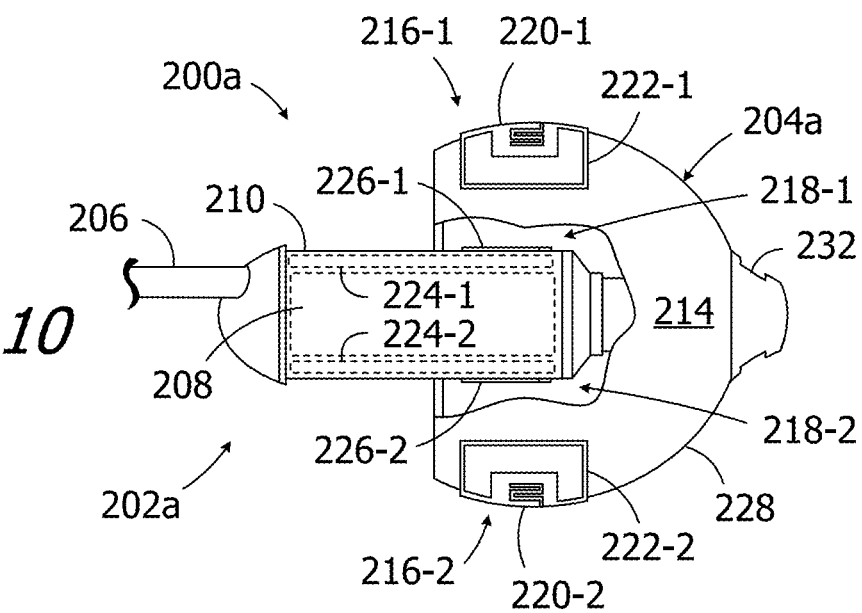
FIG. 10 is a side cutaway view of the ITE component of a hearing device in accordance with one embodiment of a present invention.

For example, as the earpiece 214 presses the sensor apparatus 216 against the ear canal EC (FIG. 3), voltage difference over time between two electrical contacts is recorded as illustrated in FIG. 5 to produce an ECG wave. The electrical contacts may be on the same sensor apparatus 216, or there may be a single electrical contact on each of two sensor apparatuses that are carried on the same earpiece 214 (as is discussed below with reference to FIG. 10). The RFID signal may be turned OFF at the end of the P wave and turned on after the R peak to transmit the biomarker data sensed during the R peak. The time between the beginning of one RFID outage and the next RFID outage is, accordingly, equivalent to the R-R interval $T_R$.

It should be noted here that the RFID sampling rate must be faster than the frequency of the sensed biomarkers. Nyquist sampling rates may, for example, be employed. Also, when OOK is employed in the manner described above and below, actual bio-marker data is not transferred in the RFID signal. Instead, OOK is used to measure the timing of the associated biomarker. This limits the type of measurements that can be made when OOK is employed. For example, biomarkers such as temperature that requiring precise level of measurements may in at least some instances require a different data transmission technique (e.g., multi-level encoding to represent bits other than 0 and 1) or a wired connection between sensor apparatus and the reader.

Figure 5A:
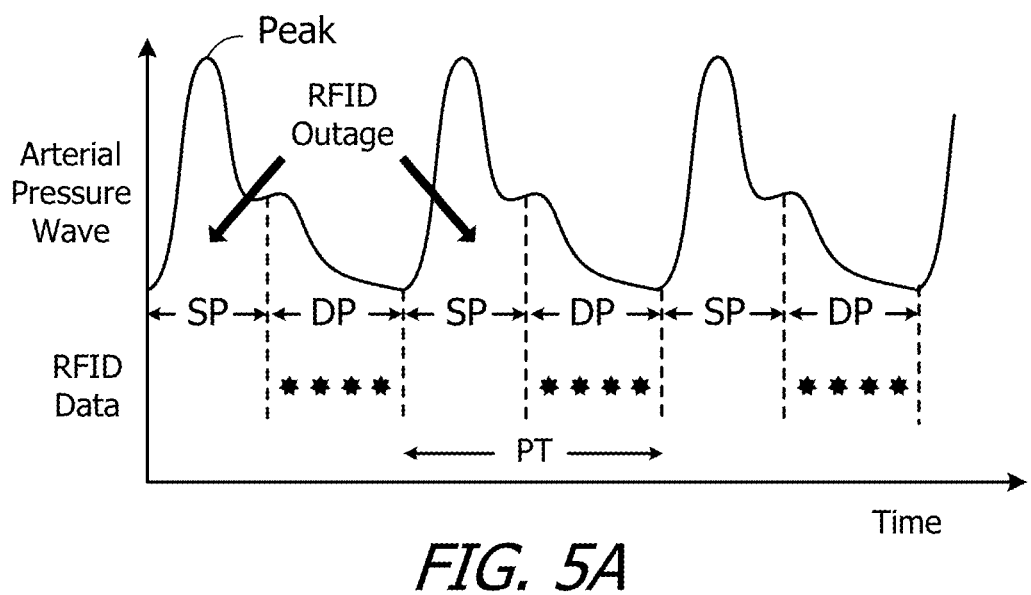
FIG. 5A is a graph showing sensed biomarker and an exemplary communication technique that may be used by the hearing system illustrated in FIG. 1.

Arterial pressure is another exemplary biomarker, as is noted above, and the receiver assembly 202 and earpiece assembly 204 may be used to obtain arterial pulse measurements. Arterial pulses will create pressure variances on the strain gauge or other mechanical sensor apparatus. An exemplary arterial pressure wave is illustrated in FIG. 5A. Here, the sensor apparatus 216 may include a strain gauge, the sensor apparatus may be configured to resonate at the reader resonant frequency when the strain gauge is in a particular mechanical state (e.g., a relaxed state due to normal arterial pressure) and to resonate at a frequency other than the resonant frequency when the strain gauge is in a different mechanical state (e.g., a strained state due to high arterial pressure). Thus, in this example, the signal will be in an ON state when the sensed arterial pressure is normal and will be in an OFF state when the sensed arterial pressure is high. The RFID signal may be turned OFF at the beginning of the systolic phase SP and turned ON at the beginning of the diastolic phase DP to transmit the biometric information sensed during the systolic phase SP. This may be accomplished by detecting a drop in pressure level. The time between the beginning of one RFID outage and the next RFID outage is, accordingly, equivalent to that of the arterial pulse PT.

Referring to FIGS. 6-9, and as noted above, the exemplary ITE component 200 includes the receiver assembly 202 as well as the earpiece assembly 204 that is mounted on the receiver assembly. The active reader circuit 224 of the reader 218 (FIG. 8) is located within the receiver housing 210, as is the receiver 208, while the reader antenna 226 is located on the exterior of the receiver housing and is electrically connected to the reader circuit 224. In other implementations, the reader circuit 224 may be located on the exterior of, or be otherwise attached to, the receiver housing 210. For example, the reader circuit 224 may be printed onto the exterior of the receiver housing 210 using molded interconnect device ("MID") techniques. Turning to the earpiece assembly 204, the earpiece 214 includes a dome-shaped wall 228, a connector 230, one or more sound outlets 232, and a short lumen 234 between the sound outlet and the connector. The connector 230 mates with a corresponding connector 236 on the receiver assembly sound tube 212 to secure the earpiece assembly 204 to the receiver assembly 202 in the manner illustrated in FIGS. 6 and 7, thereby positioning the end of the sound tube 212 in or adjacent to the lumen 234. The connector 230 and connector 236 are configured to mount the earpiece assembly 204 onto the receiver assembly 202 in such a manner that the earpiece assembly is removably secured to the receiver assembly, i.e., can be removed and replaced as necessary or desired without damage to the receiver assembly. The earpiece assembly 204 may be permanently secured to the receiver assembly 202 in other implementations. Additionally, in some instances, a pressure equalization aperture 238 may extend through the wall 228 to facilitate placement of the earpiece 214 within the ear canal.

The earpiece assembly 204 may be mounted on the receiver assembly 202 such that the antennas 222 and 226 are aligned with one another and face one another through the earpiece wall 228. Referring to FIGS. 7 and 8, the reader antenna 226 is positioned under the sensor apparatus antenna 222. In some instances, structures may be provided on the receiver assembly 202 and the earpiece assembly 204 to ensure that the antennas are positioned in the intended orientation relative to one another (e.g., the orientation shown in FIGS. 7 and 8). For example, the connector 230 and connector 236 may be mechanically keyed so as to prevent the earpiece 214 from being mounted onto the sound tube 212 in anything other than the intended orientation Suitable materials for the earpiece 214 include elastomeric material having compliance properties (and dimensions) configured to conform to the shape of the intended portion of the ear canal and exert a spring force on the ear canal so as to hold the receiver assembly 202 in place in the ear canal and press the sensor 216 against tissue within the ear canal for biometric sensing. Exemplary foams, both open cell and closed cell, include but are not limited to foams formed from polyurethanes, silicones, polyethylenes, fluoropolymers and copolymers thereof.

The configuration of the sensor apparatus 216 (including the sensor 220 and antenna 222) may be such that the sensor apparatus conforms, or at least substantially conforms to the curvature of the outer surface of earpiece 214. The flexibility of the sensor apparatus 216 may be such that the sensor apparatus assumes the curvature of the outer surface of earpiece 214 as the sensor is attached to the earpiece, as is the case in the illustrated implementation. The sensor apparatus 216 can also conform to the ear canal as the earpiece is compressed therein. In other implementations, the sensor apparatus may be stiffer and pre-curved prior to placement on the earpiece.

The ITE components may also include two or more sensor apparatuses. One example of such an earpiece assembly is generally represented by reference number 200a in FIG. 10. ITE component 200a is essentially identical to ITE component 200 and similar elements are represented by similar reference numerals. For example, the exemplary ITE component 200a includes a receiver assembly 202a with a housing 210 and an earpiece assembly 204a with an earpiece 214. Here, however, two sensor apparatuses 216-1 and 216-2 with sensors 220-1 and 220-2 and antennas 222-1 and 222-2 are carried on the earpiece 214, and corresponding readers 218-1 and 218-2 with antennas 226-1 and 226-2 are carried on the receiver assembly housing 210. The sensors 220-1 and 220-2 may be the same (as illustrated), they may be different, they may sense the same biomarker at two different locations within the ear canal, they may combine to sense a single biomarker, and/or they may sense different biomarkers. For example, each sensor 220-1 and 220-2 may be an electrical contact, and the two electrical contacts may together define an electrical contact pair used to sense an ECG wave. The sensor apparatus antennas 222-1 and 222-2 are respectively aligned with the reader antennas 226-1 and 226-2. By way of example, but not limitation, the sensor apparatuses 216-1 and 216-2 are located on opposite sides of the earpiece 214, i.e., are offset by 180 degrees, while the reader antennas 226-1 and 226-2 are correspondingly located on opposite sides of the housing 210. Both of the reader antennas 226-1 and 226-2 are connected to the active reader circuits 224-1 and 224-2 within the housing 210. The sensor apparatus 216-1 and reader 218-1 may also operate at a different frequency than the sensor apparatus 216-2 and reader 218-2. The signals from sensors sensor 220-1 and 220-2 that measure the same biomarker may also be combined by the associated external data processor 300 (discussed below with reference to FIG. 13) to improve signal quality.

Figure 11:
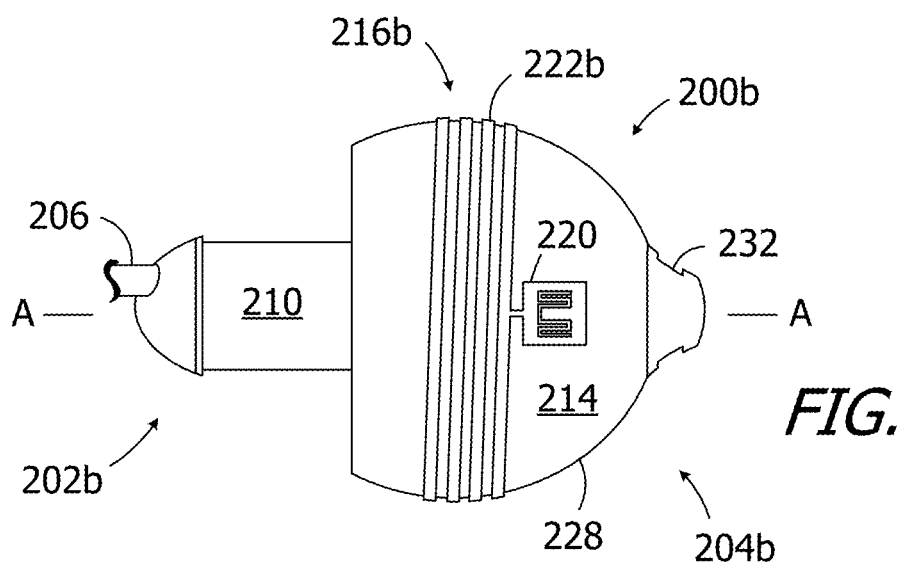
FIG. 11 is a side view of the ITE component of a hearing device in accordance with one embodiment of a present invention.
Figure 12:
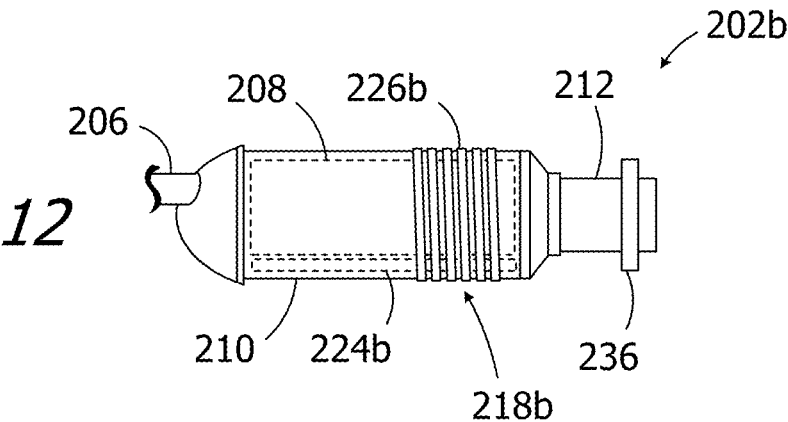
FIG. 12 is a side view of a portion of the ITE component illustrated in FIG. 11.

Another exemplary ITE component 200b is illustrated in FIGS. 11 and 12. ITE component 200b is essentially identical to ITE component 200 and similar elements are represented by similar reference numerals. For example, the exemplary ITE component 200b includes a receiver assembly 202b with a housing 210 and an earpiece assembly 204b with an earpiece 214, and a sensor apparatus 216b on the earpiece assembly communicates with a reader 218b on the receiver assembly. The reader 218b includes a reader circuit 224b and an antenna 226b. Here, however, the sensor apparatus antenna 222b and the reader antenna 226b each have a helical shape. The helical antennas 222b and 226b each have one or more turns that extend completely around the receiver assembly housing 210 and the earpiece 214. As a result, the relative orientation of the receiver assembly 202b and the earpiece assembly 204b around the earpiece assembly axis A is less of an issue than it is in the case of the ITE components 200 and 200a described above.

Figure 13:
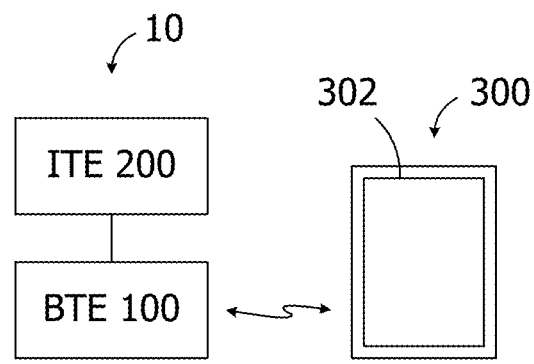
FIG. 13 is a block diagram of a system in accordance with one embodiment of a present invention.

The present hearing devices may in some instances be used in conjunction with an external data processor such as a smartphone or a computer (e.g., a tablet or laptop). The external data processor may include applications that facilitate analysis of the biometric data. In addition to processing the biometric data, the external data processor may be used to convey biometric information (or related information) in audible and/or visible form through the use of speakers, buzzers, lights, displays and the like. Referring to FIG. 13, the exemplary hearing device 10 may be connected to an external data processor 300 with a touch screen display 302 through the use of a wireless connection (as shown) or a wired connection. One exemplary wireless connection is a Bluetooth wireless connection. The external data processor 300 may also be used to transfer the sensed biometric data to health care provider, emergency medical service, and telehealth platforms.

Figure 14:
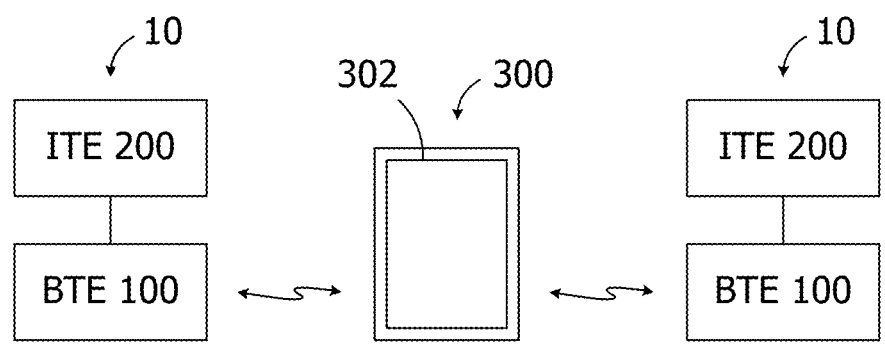
FIG. 14 is a block diagram of a system in accordance with one embodiment of a present invention.

Similarly, a pair of hearing devices 10 are employed in the right and left ears in a binaural arrangement (FIG. 14), and both of the hearing devices may be connected to the external data processor 300 through the use of a wireless connection (as shown) or a wired connection. The sensors 220 of the respective ITE components 200 may be the same, they may be different, they may sense the same biomarker in two different ear canals, they may combine to sense a single biomarker from different ear canals, they may sense different biomarkers, and/or they may operate at a different frequencies. The signals from sensors 220 in each ear that measure the same biomarker may also be combined by the external data processor 300 to improve signal quality.

Figure 15:
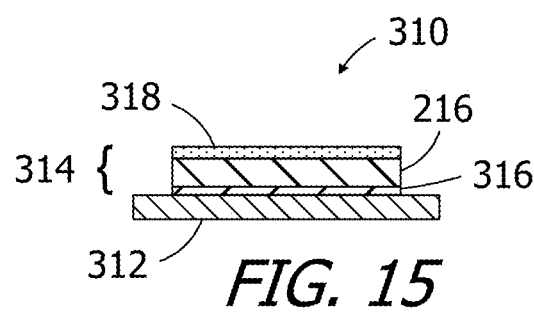
FIG. 15 is a section view of an aspect of an exemplary process.

Any suitable process may be used to position sensor apparatuses onto soft earpieces. In one exemplary process, a sensor apparatus may be carried on a thin film and transferred to an earpiece as part of the earpiece molding process. Such a process is similar to an in-mold decoration process. For example, the sensor apparatus carrier 310 illustrated in FIG. 15 may be used in the earpiece molding process illustrated in FIGS. 16-19. The exemplary carrier 310 includes a carrier film 312 on which sensor units 314 are formed. Each sensor unit 314 may include a separation layer 316, a sensor apparatus 216 and a bonding layer 318. The sensor apparatus 216, which is flexible and stretchable, may be formed from conductive printable materials such as silver nanoparticles, polypyrrole nanoparticles, Graphene-based materials, carbon nanotube-based materials, copper-based materials and/or gold-based materials using inkjet printing methods.

The carrier film 312 with sensor units 314 may be fed into, for example, the exemplary injection mold system 320 with mold parts 322 and 324, a roller system 326, clamps 328 and ejectors 330. The mold part 322 includes a recess 332, while the mold part 324 includes a protrusion 334 and an injection port 338. The recess 332 and projection 334 together define a mold cavity 336 (FIG. 18) when the mold parts 322 and 324 are brought together. It should be noted here that the injection mold system 320 is shown in simplified form for purposes of explanation, and that various details of the system (e.g., the mold parts) and the resulting earpieces have been omitted from this discussion for the sake of simplicity.

Figures 16, 17:
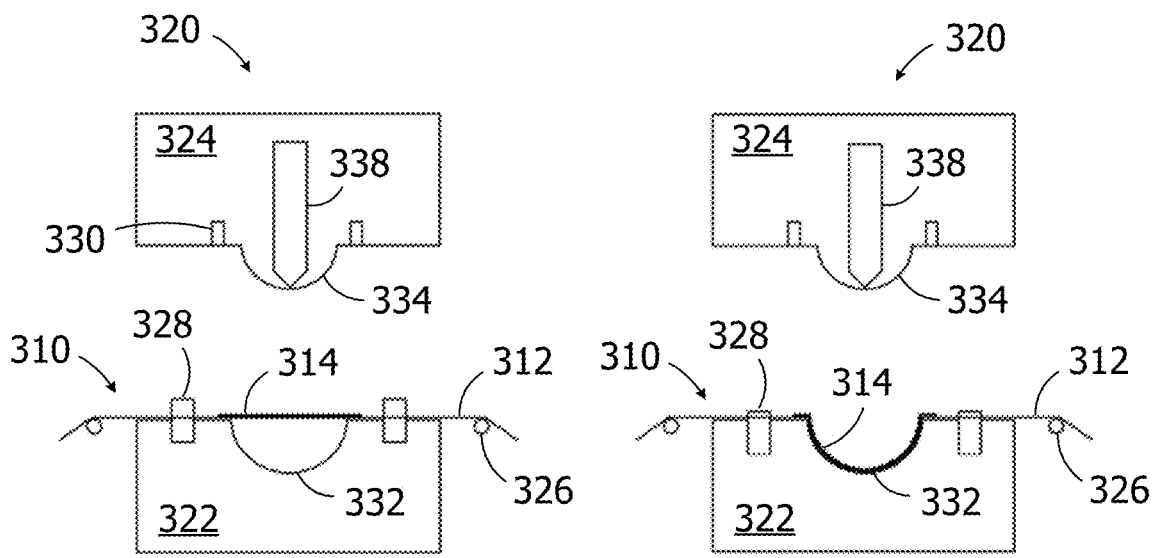
FIGS. 16-19 are diagrammatic view of an exemplary process.
Figures 18, 19:
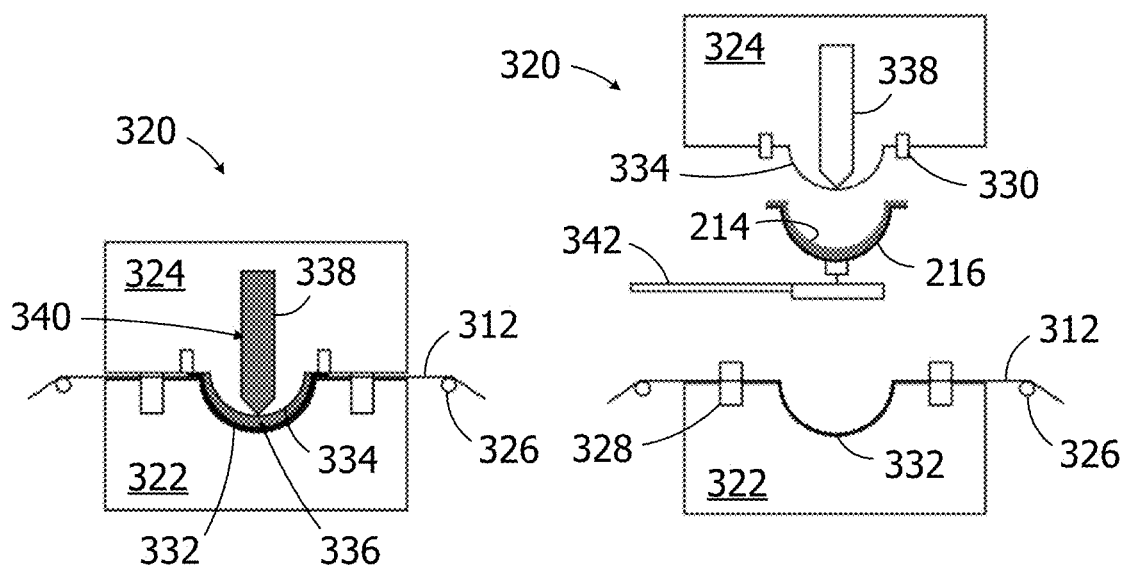

Referring more specifically to FIG. 16, the initial step of the process is to advance the carrier film 312 relative to the mold parts 322 and 324 until a sensor unit 314 is aligned with the recess 332 and projection 334. Turning to FIG. 17, the carrier film 312 may then be fixed in place by clamps 328, and the sensor unit 314 (and corresponding portion of the film 312) may be pulled against the surface of the recess 332 by a vacuum port (not shown). The mold parts 322 and 324 may then be brought together to form the mold cavity 336, as is illustrated in FIG. 18, and the elastomeric foam material 340 may be injected into the mold cavity. The heat from the injection process will cause the sensor apparatus 216 to adhere to the foam material and release from the carrier film 312 and separation layer 316. The ejectors 330 may then be used to separate the earpiece 214 from the mold protrusion 334 and to deposit the earpiece 214 (with sensor apparatus 216) onto a carrier 342. The clamps 328 may then be opened so that the carrier film 312 can be advanced and the next sensor apparatus 216 aligned with the mold recess 332.

Although the inventions disclosed herein have been described in terms of the preferred embodiments above, numerous modifications and/or additions to the above-described preferred embodiments would be readily apparent to one skilled in the art. By way of example, but not limitation, the present inventions may be practice with ITE hearing instrumentalities that do not include earpieces. Such ITE hearing instrumentalities include those with housings that are molded into the size and shape of the wearer's ear canal, and the present sensors may be mounted on the exterior of the housing. The inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. An in-the-ear ("ITE") hearing instrumentality for use in an ear canal, comprising:
   a receiver housing;
   a receiver located within the receiver housing;
   at least one biometric sensor; and a soft foam earpiece, having an outer surface on which the biometric sensor is located, that is removably secured to the receiver housing and is configured to conform to the shape of the ear canal and to apply a spring force on the ear canal such that the soft foam earpiece mounts the receiver housing within the ear canal and presses the biometric sensor against tissue within the ear canal.

2. The ITE hearing instrumentality of claim 1, wherein the biometric sensor is part of a sensor apparatus that includes the biometric sensor and an antenna connected to the biometric sensor.

3. The ITE hearing instrumentality of claim 2, wherein the biometric sensor comprises a passive biometric sensor.

4. The ITE hearing instrumentality claimed in claim 1, wherein
the at least one biometric sensor on the earpiece comprises a plurality of biometric sensors on the earpiece.

5. The ITE hearing instrumentality claimed in claim 1, wherein
at least one biometric sensor is a capacitive sensor or a resistive sensor.

6. The ITE hearing instrumentality claimed in claim 1, wherein
the biometric sensor is configured to sense a biomarker selected from the group consisting of arterial pressure, arterial pulse peaks, electrical signals used in an electrocardiogram ("ECG"), heart rate, heart rate variability, oxygen level, blood pressure, hydration, galvanic skin response, and the presence, absence, level or concentration of particular chemicals, enzymes, proteins or drugs.

7. A hearing device, comprising:
an ITE hearing instrumentality as claimed in claim 1; and
a behind-the-ear ("BTE") component, operably connected to the ITE hearing instrumentality, that includes a BTE housing, a microphone and a processor.

8. The hearing device of claim 7, wherein
the BTE component is connected to the ITE hearing instrumentality by a wired connection.

9. The ITE hearing instrumentality claimed in claim 1, wherein
the biometric sensor is flexible and conforms to shapes of earpiece and the ear canal.

10. The ITE hearing instrumentality claimed in claim 1, wherein
the receiver housing includes a sound tube and a connector on the sound tube; and
the soft foam earpiece includes a dome-shaped wall and a connector that mates with the connector on the sound tube.

11. An in-the-ear ("ITE") hearing instrumentality for use in an ear canal, comprising:
a receiver housing;
a receiver located within the receiver housing;
an earpiece on the receiver housing that is configured to mount the receiver housing within the ear canal;
a sensor apparatus, that includes at least one passive biometric sensor and an antenna connected to the passive biometric sensor, on the earpiece; and
an active reader associated with the receiver housing.

12. The ITE hearing instrumentality of claim 11, wherein
the receiver housing includes an interior and an exterior; and
the active reader includes a reader circuit within the receiver housing interior and an antenna, connected to the reader circuit, on the receiver housing exterior.

13. The ITE hearing instrumentality claimed in claim 12, wherein
the antenna on the earpiece and the antenna on the receiver housing exterior face one another through the earpiece.

14. A method, comprising the step of:
sensing a first biomarker within a first ear canal with a first biometric sensor that is pressed against tissue within the first ear canal by a removable soft foam earpiece that is on a receiver housing of a first in-the-ear ("ITE") hearing instrumentality.

15. The method of claim 14, further comprising the step of:
sensing a second biomarker within the first ear canal with a second biometric sensor that is pressed against the first ear canal by the portion of the first ITE hearing instrumentality.

16. The method of claim 15, wherein
the first and second biomarkers are different biomarkers.

17. The method of claim 14, further comprising the step of:
sensing a second biomarker within a second ear canal with a second biometric sensor that is pressed against the second ear canal by a portion of a second ITE hearing instrumentality.

18. The method of claim 17, wherein
the first and second biomarkers are different biomarkers.

19. The method claimed in claim 17, wherein
the second ITE hearing instrumentality includes an earpiece; and
the second biometric sensor is pressed against the second ear canal by second ITE hearing instrumentality earpiece.

20. The method claimed in claim 14, wherein
the first biomarker is selected from the group consisting of arterial pressure, arterial pulse peaks, electrical signals used in an electrocardiogram ("ECG"), heart rate, heart rate variability, oxygen level, blood pressure, hydration, galvanic skin response, and the presence, absence, level or concentration of particular chemicals, enzymes, proteins or drugs.

21. A method, comprising the step of:
sensing a first biomarker within a first ear canal by pressing a passive first biometric sensor against tissue in the first ear canal with a portion of a first in-the-ear ("ITE") hearing instrumentality and interrogating the passive first biometric sensor with an active reader on the first ITE hearing instrumentality.

* * * * *